US007062714B1

(12) United States Patent
Mo et al.

(10) Patent No.: US 7,062,714 B1
(45) Date of Patent: Jun. 13, 2006

(54) IMAGING SYSTEM HAVING PRESET PROCESSING PARAMETERS ADAPTED TO USER PREFERENCES

(75) Inventors: Larry Y. L. Mo, Waukesha, WI (US); Dean W. Brouwer, Muskego, WI (US); Terry J. Duesterhoeft, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 921 days.

(21) Appl. No.: 09/628,173

(22) Filed: Jul. 28, 2000

(51) Int. Cl.
*G06F 3/01* (2006.01)

(52) U.S. Cl. ........................ 715/731; 715/764; 715/831; 715/780; 715/767; 358/474

(58) Field of Classification Search ................ 345/700, 345/731, 764; 382/162–172; 715/700, 731, 715/764, 780, 767; 358/474, 498
See application file for complete search history.

(56) References Cited

U.S. PATENT DOCUMENTS

| 4,271,389 A | * | 6/1981 | Jacobi et al. ................ 324/639 |
| 5,877,819 A | * | 3/1999 | Branson ...................... 348/701 |
| 6,175,614 B1 | * | 1/2001 | Jensen et al. ............... 378/98.7 |
| 6,318,635 B1 | * | 11/2001 | Stoner .................... 235/462.45 |
| 6,318,637 B1 | * | 11/2001 | Stoner .................... 235/472.01 |
| 6,665,086 B1 | * | 12/2003 | Hull et al. .................. 358/1.15 |
| 6,665,098 B1 | * | 12/2003 | Nagarajan ................... 358/474 |

* cited by examiner

*Primary Examiner*—Weilun Lo
*Assistant Examiner*—Mylinh Tran
(74) *Attorney, Agent, or Firm*—Ostrager Chong Flaherty & Broitman P.C.

(57) ABSTRACT

An imaging system has a computer which monitors changes to any given front-panel control setting for a particular image processing parameter (e.g., dynamic range, transmit foci position, Doppler wall filter setting, etc.) as compared to its default or preset value. For each user ID (e.g., based on the system user's name or any user code) and each application type, if, over a number of exam cycles, the user is found to consistently adjust a particular control setting to values that deviate significantly from the preset value, the system computer will automatically adjust the preset value to, e.g., the average setting of that image processing parameter over the past N trials, where N is a predefined integer number.

8 Claims, 3 Drawing Sheets

IMAGING SYSTEM HAVING PRESET PROCESSING PARAMETERS ADAPTED TO USER PREFERENCES

FIELD OF THE INVENTION

This invention generally relates to ultrasound imaging for the purpose of medical diagnosis. In particular, the invention relates to methods for imaging tissue and blood flow by detecting ultrasonic echoes reflected from a scanned region of interest in a human body.

BACKGROUND OF THE INVENTION

Conventional ultrasound scanners are capable of operating in different imaging modes. In the B mode, two-dimensional images can be generated in which the brightness of each display pixel is derived from the value or amplitude of a respective acoustic data sample representing the echo signal returned from a respective focal position within a scan region.

In the B-mode imaging, an ultrasound transducer array is activated to transmit beams focused at respective focal positions in a scan plane. After each transmit firing, the echo signals detected by the transducer array elements are fed to respective receive channels of a receiver beamformer, which converts the analog signals to digital signals, imparts the proper receive focus time delays and sums the time-delayed digital signals. For each transmit firing, the resulting vector of raw acoustic data samples represents the total ultrasonic energy reflected from a succession of ranges along a receive beam direction. Alternatively, in multi-line acquisition two or more receive beams can be acquired following each transmit firing.

In conventional B-mode imaging, each vector of raw acoustic data samples is envelope detected and the resulting acoustic data is compressed (e.g., using a logarithmic compression curve). The compressed acoustic data is output to a scan converter, which transforms the acoustic data format into a video data format suitable for display on a monitor having a conventional array of rows and columns of pixels. This video data is referred herein as "raw pixel intensity data". The frames of raw pixel intensity data are mapped to a gray scale for video display. Each gray-scale image frame, hereinafter referred to as "gray-scale pixel intensity data", is then sent to the video monitor for display.

A conventional ultrasound imaging system typically employs a variety of gray maps, which are simple transfer functions of raw pixel intensity data to display gray-scale values. Multiple gray maps are supported so that different maps may be used depending on the range of pixel intensities. For example, if a given application tends to generate mainly low raw pixel intensities, then a gray map which dedicates more gray-scale values to low raw pixel intensity values is desired since it improves the contrast across this range. Therefore, it is typical to default to a different gray map depending on the application. However, this is not always effective since the user can scan any anatomy in any application, acoustic data varies from patient to patient, and the raw pixel intensity values depend on other system settings such as dynamic range and gain. Due to these factors, the gray maps tend to be conservative with respect to how many gray-scale values are dedicated to the anticipated primary pixel intensity range.

The default values of many ultrasound image processing parameters, such as dynamic range for two-dimensional image display, transmit foci positions, gain, etc., are preset in a preset menu. These preset values are often based on clinical testing aimed at achieving optimal image performance for the average or typical patient in a particular exam or application type. However, for certain classes of image processing parameters such as those affecting the display contrast, different users may have different preferences depending on application type, and furthermore, their preferences may evolve over time as they develop experience with the scanner.

In conventional scanners, there are also many image processing parameters that are not available in the preset menu; i.e., they may not be adjustable by the user. One example is the adaptive gray mapping feature for B-mode imaging, as taught in U.S. Pat. No. 6,048,311 entitled "Method and Apparatus for Ultrasound Imaging Using Adaptive Gray Mapping." This reference teaches a method which allows the system user to adjust the contrast by pressing a button on an operator interface. When the user has positioned the probe over the anatomy of interest, depressing a button triggers the host computer inside the ultrasound imaging system to retrieve the current frame of raw pixel intensity data, analyze its pixel intensity histogram within a user-specified region of interest (ROI), and then automatically scale and/or shift the gray mapping (i.e., raw pixel intensity to gray-scale pixel intensity mapping) such that pre-defined (i.e., fixed by the manufacturer) optimal upper and lower gray-scale levels map to some upper and lower bounds of the pixel intensity histogram respectively. The ultimate goal is to more fully utilize the available gray-scale levels (256 levels for an 8-bit display system) to display the pixel intensity data, thereby improving the display contrast.

The limitation with the foregoing approach is that no predefined goodness criteria, in terms of gray level limits, will satisfy all users. If the user finds the adaptive gray mapping gives too much contrast, he/she would often manually change the dynamic range or gain to counteract the gray-scale changes effected by the adaptive gray mapping feature. One solution is to make the target gray map parameters adjustable in the preset menu. But as stated above, user preferences may change with time and having additional adjustable parameters may detract from the adaptive power of the adaptive gray mapping feature.

SUMMARY OF THE INVENTION

The present invention is directed to a scanner that can determine the preferred settings of each user for selected system parameters based on a number of scanning cycles, and then automatically adjust the system "presets" to take into account those preferred settings. A scanning cycle is defined relative to use of a specific scanner feature or mode. Its beginning may be marked by the activation of a particular feature/mode control key, and its end may be defined by time elapsed and/or by another change to front-panel controls (e.g., manipulation of a Print or Save button). In accordance with the preferred embodiment of the invention, the adaptive gray mapping feature for B-mode imaging is extended so that it can automatically determine the user-desired contrast levels based on a number of scanning cycles, and then adjust its internal gray map parameters to track the user's preferences.

In its broadest scope, this invention encompasses using the system computer to monitor changes to any given front-panel control setting for a particular image processing parameter (e.g., dynamic range, transmit foci position, Doppler wall filter setting, etc.) as compared to its default or preset value. For each user ID (e.g., based on the system user's name or any user code) and each application type, if, over a number of exam cycles, the user is found to consistently adjust a particular control setting to values that deviate significantly from the preset value, the system computer will automatically adjust the preset value to, e.g., the average setting of that image processing parameter over the past N trials, where N is a predefined integer number. Alternatively, the computer may also first send a message to the monitor display to report the average value of that image processing parameter used in the past N exams, and to ask whether the user wants the preset value to be adjusted automatically as a function of that average value.

For the extended adaptive gray mapping feature, the image processing parameters are the optimal upper and lower gray levels that the image pixel intensity histogram bounds should be mapped to. The pertinent front-panel controls that may be monitored include dynamic range, gain and gray map selection. The front-panel controls for dynamic range and gain are typically manually adjustable knobs, while gray map selection in one known system involves soft-key selection from a library of gray maps. In practice, however, the user rarely changes the gray map selection. Hence, in the preferred embodiment of this invention, the following specific capabilities are proposed:

(a) the capability of learning the user's preferences based on the manual adjustments made to dynamic range and/or gain within a predefined period of time after the initial automatic gray map adjustment;

(b) the capability of self-updating its internal optimal gray level limits based on the above learning step;

(c) the capability of analyzing (e.g., taking an average) and using the result from two or more past learning experiences; and (d) the capability of storing different optimal adaptive gray map parameters for different user names and/or application types.

As the system operator uses the above extended adaptive gray mapping feature in clinical scanning, the display contrast level achieved by adaptive gray mapping will rapidly approach that preferred by the user.

DETAILED DESCRIPTION OF THE PREFERRED EMBODIMENTS

Figure 1:
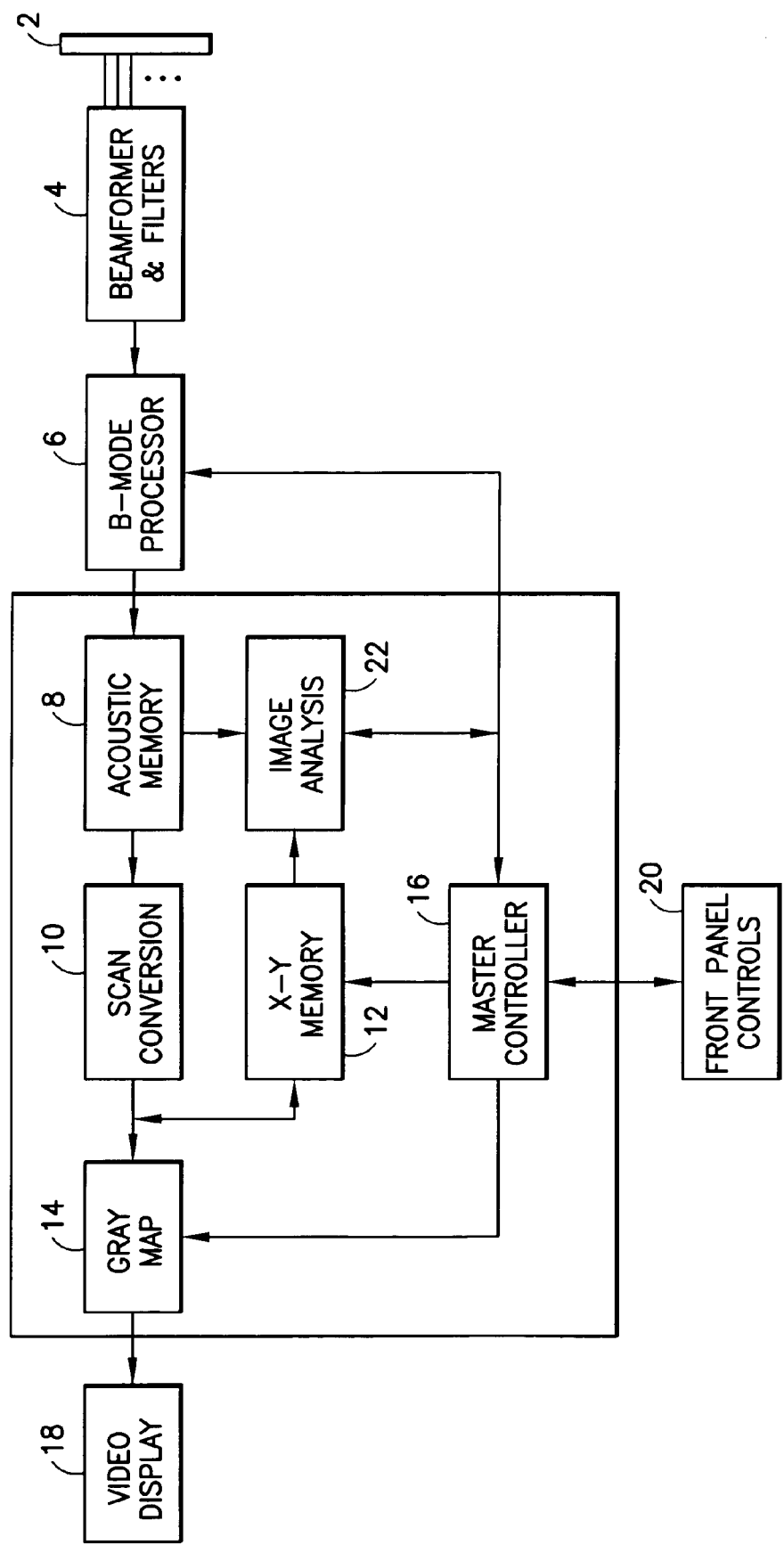
FIG. 1 is a block diagram generally showing an ultrasound imaging system in accordance with the preferred embodiment of the invention.

Referring to FIG. 1, an ultrasound imaging system in accordance with one preferred embodiment of the invention comprises a transducer array 2, and a beamformer 4 including filters. The transducer array 2 comprises a multiplicity of piezoelectric elements which are activated by a transmitter in beamformer 4 to transmit an ultrasound beam focused at a transmit focal position. The return RF signals are detected by the transducer elements and then dynamically focused at successive ranges along a scan line by a receiver in beamformer 4. The receive beamformer produces RF or equivalent I/Q data representing the echoes along each imaging beam or vector. This raw acoustic data is output to a B-mode processor 6. The B-mode processor in accordance with the preferred embodiment detects the power ($I^2+Q^2$) of the complex signal, and performs other standard filtering and transmit zone splicing operations on a vector by vector basis. The magnitude (i.e., intensity) of the signal output by the B-mode processor 6 is the square root of the power, i.e., $(I^2+Q^2)^{1/2}$. Then the B-mode amplitude data is compressed in a data compression block incorporated in the B-mode processor 6. The data compression block preferably comprises a lookup table loaded by a master controller 16 into a random access memory to reduce the dynamic range for a pixel value (typically 8 bits) display.

The compressed acoustic data is fed to the system back end, which includes an acoustic line memory 8, a scan converter 10, an X-Y memory 12, a gray map processor 14, and a master controller 16 which coordinates the activities of all the functional blocks of the scanner. The acoustic line memory 8 accumulates vectors of compressed acoustic data for one sweep across the array and interpolates where necessary to form a two-dimensional image. The scan converter 10 transforms the R-θ or X-Y acoustic data format into an X-Y pixel or video data format by coordinate transformation, thus forming the pixel intensity data, which is stored in the X-Y display memory 12.

The scan-converted frames are passed to a video processor 14, which converts the pixel intensity data to the video frame rate and then maps the pixel intensity data to a gray-scale mapping for video display. A conventional ultrasound imaging system typically employs a variety of gray maps, which are simple transfer functions of the raw pixel intensity data to display gray-scale levels. Preferably the gray maps take the form of lookup tables loaded into random access memory by the master controller 16. The gray-scale image frames are then sent to the display monitor 18 for display.

System control is centered in the master controller 16, which accepts operator inputs through an operator interface, e.g., front panel controls 20, analyzes the acquired data and controls the various subsystems based on operator inputs and the results of data analysis. In accordance with the preferred embodiment, the master controller 16 performs one or more of the following functions: (1) providing transmit and beamforming parameters to the beamformer 4; (2) providing a new gray map to the video processor 14; (3) retrieving an image frame from X-Y memory 12, re-scaling that image frame and then sending the re-scaled image to the display monitor for display in a zoom mode; and (4) providing a new data compression curve to the B-mode image processor 6. Preferably, the gray map, beamforming parameters and compression curves are provided in the form of lookup tables stored in random access memory. Although FIG. 1 depicts separate paths for the communications to and from the master controller 16, it will be readily appreciated that these communications may take place over a common channel or system bus.

In accordance with a known adaptive gray mapping capability, the system user can initiate adjustment of the display contrast by pressing a front panel control button 20. Key to the adaptive gray mapping feature is an image analysis function 22, which can grab image frames from either the acoustic memory 8 or the X-Y memory 12, and then effect system parameter changes via the master controller 16.

All of the data processing blocks inside the dashed box in FIG. 1 (namely, scan conversion 10, gray mapping 14, master controller 16 and image analysis 22 can be implemented as different software programs running on a computer.

In accordance with the adaptive gray mapping function, a new image frame is read out by the image analysis block 22 directly from the X-Y display memory 12 or the acoustic line memory 8. The image pixel intensity histogram is computed within a predefined ROI (e.g., a large central ROI within the image frame) by the image analysis block 22. The histogram data is stored in buffer memory in the image analysis block. The image analysis block determines the upper and lower bounds of the stored pixel intensity histogram. The master controller 16 scales and/or shifts the gray map (i.e., raw pixel intensity to gray-scale pixel intensity mapping) such that pre-defined optimal upper and lower gray-scale levels map to the upper and lower bounds of the stored pixel intensity histogram. Such a gray map adjustment is basically known in the art, but will be described later in detail for the sake of completeness.

Figure 2:
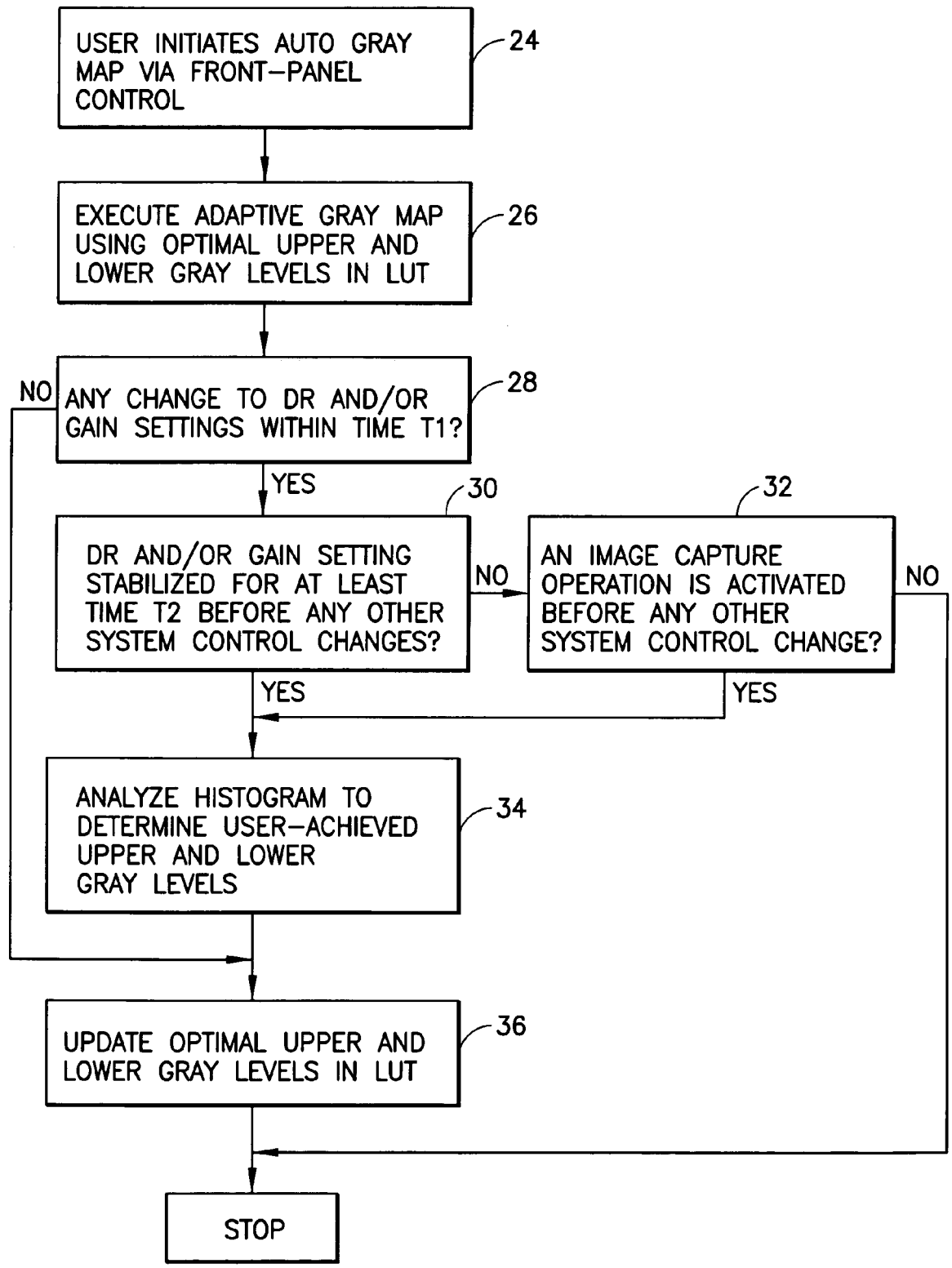
FIG. 2 is a flowchart showing the steps of an algorithm for monitoring user preferences for display contrast level and automatically adapting gray mapping presets as a function of those user preferences in accordance with the preferred embodiment of the invention.

The preferred embodiment of the present invention involves an extension of the adaptive gray mapping optimization feature. However, the invention in its broad scope has application with other adaptive imaging parameters. The extended gray mapping feature involves mainly the image analysis, master control and gray mapping functions (blocks 22, 16 and 14 in FIG. 2. The optimal upper and lower gray level settings are stored in an optimal gray map parameter lookup table (LUT) for each application type and user ID (e.g., doctor's or sonographer's name or ID). The basic steps of this adaptive gray mapping feature (shown in FIG. 2) are detailed as follows.

The user initiates adaptive gray-scale adjustment by pushing an adaptive gray map optimization button on the front-panel control (step 24). In response to this operator input, the image analysis block grabs the current image frame from the X-Y memory (or the acoustic line memory), and analyzes its pixel intensity histogram over a predefined region of interest (ROI), such as a large central region of the image. Based on the actual histogram upper and lower bounds (defined, for example, by the 95th and 5th percentile points respectively), the image analysis block instructs the master controller to re-scale the gray map such that the upper and lower histogram bounds are mapped to the optimal upper and lower gray levels, as specified in the optimal gray map parameter LUT (step 26).

After the adaptive gray scale adjustment, the master controller begins to monitor (step 28) changes to the front-panel gain and dynamic range (DR in FIG. 2) controls for a predefined time period T1 (e.g., 3 seconds). It is assumed that the user will change either the gain or dynamic range setting within time period T1 if he/she is not completely satisfied with the automated adjustment performed in step 26. If no front-panel changes are detected within time period T1, it is assumed that the user is satisfied with the adaptive gray map adjustment. In this case the learning process is terminated and the system proceeds to step 36, i.e., the optimal gray map parameter LUT is updated. This is accomplished by writing the current (however achieved) upper and lower gray levels to a new row or entry in the optimal gray map parameter LUT.

If front-panel changes to the gain or dynamic range settings are detected within the time period T1 (step 28), it is assumed that the user is not completely satisfied with the adaptive gray map adjustment performed in step 26 and has made further manual adjustment(s). The changes are continuously monitored (step 30) by the master controller until these dynamic range and/or gain changes are stabilized for at least a time period T2 (e.g., 15 sec.) If the master controller detects stabilized settings, the master controller proceeds to step 34.

If an image capture control, which may be defined by one of a plurality of front-panel keys such as FREEZE, PRINT or SAVE, is activated before any other system control is changed (step 32), then the manual adjustments are considered good and the learning process continues, i.e., the master controller proceeds to step 34.

If however, before the time period T2 has expired, some system control such as application type or imaging mode is changed, then it is ambiguous as to whether the user is satisfied with the adaptive gray map result. In this situation, the present scanning cycle will be simply ignored (i.e., not recorded as an entry in the optimal gray map parameter LUT) and the learning process is terminated until another scanning cycle is initiated by the user.

In step 34, the pixel intensity histogram of the manually adjusted image frame is analyzed to see what gray levels its upper and lower bounds are now mapped to. The user-selected upper and lower gray levels are considered to be the more desirable gray levels to the user than the LUT values. The optimal gray map parameter LUT is updated (step 36) as previously described (i.e., by writing the current upper and lower gray levels to a new row or entry in the optimal gray map parameter LUT. Alternatively, a moving average of the most recent N entries may be computed to obtain the new optimal upper and lower gray levels.

As an additional option, some user's control, such as a software key, can be provided to turn the above update or "learning" mode on or off. There will be times when the user wants to operate the system with more extreme settings to maximize the contrast around an unusual lesion, or perhaps for teaching or system maintenance purposes. In those situations it would be desirable to have the learning mode turned off.

In yet another option, if in the adaptive gray map learning mode, the system detects a very large change in the dynamic range and/or gain settings from what the user normally uses, the system may prompt the user to confirm if he/she wishes to record these parameters to the optimal gray map parameter LUT.

In practice, a system user must input a user ID and an application or examination type at the start of an examination. In response to that inputted information, the system will automatically preset the image processing parameters, including the optimal gray map parameters, which will be retrieved from the optimal gray map parameter LUT.

Figure 3:
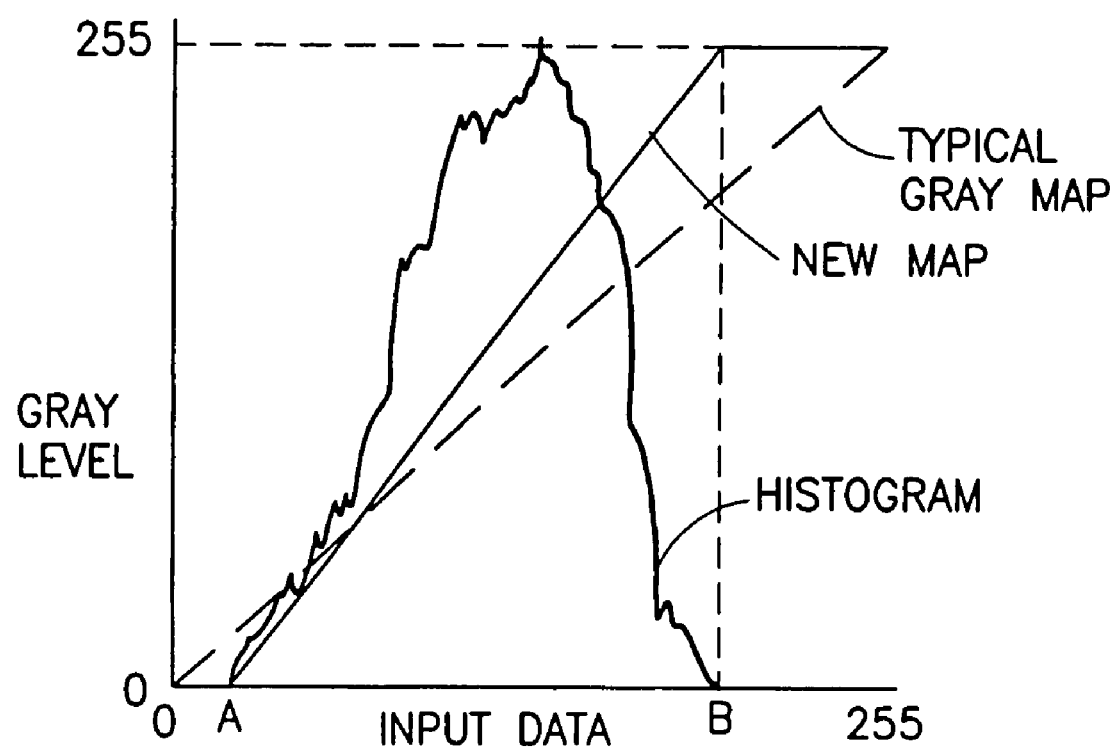
FIG. 3 is a graph showing conventional and adaptively generated gray maps superimposed on a pixel intensity histogram. For the histogram only, the pixel intensity values are plotted along the horizontal axis and the number of occurrences within each bin are plotted along the vertical axis.

The procedure for adjusting the gray map based on pixel intensity histogram data will be described in more detail. In accordance with the adaptive gray mapping function, a new image frame is read out by the image analysis means 22 directly from the X-Y display memory 12. Alternatively, the image frame could be read from the acoustic line memory 8. The image pixel intensity histogram is computed within a predefined ROI (e.g., a large central ROI within the image frame) by the image analysis means 22. Computing a histogram involves the steps of dividing the range of possible pixel intensity values into a series of non-overlapping bins of equal length, assigning each pixel intensity value in the image frame to a respective bin having that value, and counting the number of pixels in each bin for that image frame. FIG. 3 shows a graph, labeled "Histogram", of the number of occurrences (y-axis) as a function of pixel intensity values (x-axis). For an 8-bit pixel display, the smallest pixel value is zero and the largest pixel value is 255. To reduce statistical variability, the pixel bin size of the pixel intensity histogram can be set larger than unity (e.g., 5). Successive histograms are stored in buffer memory (not shown).

For the purpose of this illustration, it will be assumed that the unadjusted gray map is a linear mapping as indicated by the inclined dashed line superimposed on the histogram in FIG. 3. This gray map outputs a gray-scale value equal to the input value. Given the raw data and the gray map indicated by the dashed line in FIG. 3, roughly 171 (20 through 190) gray-scale values out of 256 (0 to 255) are used. For this example, 67% of the gray-scale values are used. It will further be assumed that the histogram shown in FIG. 3 is the currently stored histogram derived from the current image frame. The image analysis block 22 determines the upper and lower bounds of the stored pixel intensity histogram, and outputs that data to the master controller. The master controller 16 scales and/or shifts the unadjusted gray map such that the upper and lower gray-scale levels map to the upper and lower bounds of the stored pixel intensity histogram. The adaptive gray mapping feature is designed to provide a more optimal gray mapping in such circumstances, such as the new gray map indicated by the inclined solid line in FIG. 3. This new gray mapping will be loaded into the video processor 14 by the master controller 16 (see FIG. 1). The raw pixel intensity data will be contrast adjusted in video processor 14 by transforming each value into the corresponding gray-scale value established by the new gray map. The raw pixel intensity values outside the new gray map input range are mapped to a minimum (0) or a maximum (255) gray-scale value. As a result, the contrast of the raw pixel intensity data of greatest interest is increased.

As previously described, the analysis of the pixel intensity data in an image frame is performed by the image analysis block 22. The image analysis block 22 determines the end points of the histogram by searching from each direction. The range of raw pixel intensity values between the end points is the map input range. The master controller 16 then compresses (or expands) an existing gray map to fit the new map input range, e.g., the end points 0 and 255 of the gray-scale value range are correlated to the end points of the new map input range. Each raw pixel intensity value is then assigned a gray-scale value in accordance with this newly generated gray map. Alternatively, rather than searching for the absolute end (first non-zero input bin) from each direction, the search from each end can continue until some percentage of the raw pixel intensity data has been found. If different criteria are used at the lower and higher ends, this enables clipping of the raw pixel intensity data having the lowest and the highest values. In accordance with further variants, the end points of the histogram can be established by calculating the standard deviation of the data and finding the end points associated with a particular number of standard deviations. Rather than transforming the old map into the new map using the end points of the new map input range, it is possible to generate an entirely new map between the end points of the new map input range. Alternatively, a multiplicity of gray maps can be stored in memory, the master controller selecting the most suitable one of the stored maps and sending it to the video processor 14 which performs the gray-scale mapping.

As stated above, a new gray map can be generated by transforming an old gray map comprising a table of input and output values. In the case where the old map is a linear function, the new map will also be a linear function. Alternatively, if the old map is a nonlinear function, then the new map generated from the old map will also be a nonlinear function. For example, if the old gray map is a nonlinear function, a map transformation algorithm is used to compress (or expand) that nonlinear function to fit within the new map input range, e.g., the range from A to B in FIG. 3.

More specifically, each input value $x_{new}$ of the new map is processed to arrive at a corresponding new map output value $y_{new}$. The master controller performs the following steps.

If $x_{new} < A$, then $y_{new} = 0$.

If $x_{new} > B$, then $y_{new} = 255$.

If $A \leq x_{new} < B$, then $y_{new} = y_{old}$     (I)

where I is an index computed by the computer based on the following equation:

$$\left(1 + \frac{256 - (B-A)}{B-A}\right)(x_{new} - A) = I$$

where the number 256 represents the old map input range, and (B-A) represents the new map input range. The new map output value $y_{new}$ is obtained by inputting the index I into the old gray map to obtain the corresponding old map output value. The latter value is then transferred into the new map. This process is repeated until output values for all of the new map input values between the end values A and B have been derived from the old map. Using this technique, the old map can be compressed (or expanded) to fit within the new map input range determined from the raw data histogram.

Rather than searching for the absolute end (first non-zero input bin) from each direction, the search from each end can continue until some percentage of raw data is found. If different criteria are used at the lower and higher ends, this enables clipping of, for example, the lowest 5% of raw data and the highest 0.3% of raw data. This technique can be applied in the transformation of an old gray map (using the map transformation algorithm described above) or in the creation of a new gray map.

Alternatively, the end points can be established by calculating the standard deviation of the raw data and then finding the end points associated with a particular number of standard deviations. There is no restriction that the same criteria be used at each end.

Although the preferred embodiments have been described with reference to gray map generation by a system computer, it will be appreciated by persons skilled in the art that, in the alternative, the new gray map could be generated by dedicated hardware.

In accordance with another preferred embodiment, the data compression curve is automatically optimized (e.g., set to values which optimize contrast in the displayed image). This is preferably accomplished by writing a new data compression lookup table into random access memory in the data compression block of the B-mode processor 6. The host computer may select a suitable data compression lookup table from a multiplicity of pre-stored tables or may generate a new data compression lookup table. The data compression curve (which is typically a logarithmic function) can be optimized by itself or in combination with optimization of the gray-scale mapping function. For example, if the 90-th percentile point of the pixel intensity histogram is found to be approaching 255, the image display is likely to be saturated with blooming white pixels. In this case, the input dynamic range of the compression curve may be automatically increased to accommodate the large pixel values before further gray map adjustments are made.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An imaging system comprising:
a display monitor;
an operator interface comprising a first control input device for activating adaptive grayscale adjustment, a second control input device for setting gain, a third control input device for setting dynamic range, and a fourth control input device for activating image capture;
a scanning subsystem for acquiring raw data; and
an image processing system for processing acquired raw data to display an image frame of imaging data on said display monitor, said image processing system comprising memory for storing displayed image frames, grayscale mappings, upper and lower grayscale levels for use in adaptive grayscale adjustment, gain settings, and dynamic range settings, and a computer programmed to perform the following steps:
(a) controlling said display monitor to display an image frame of imaging data derived from acquired raw data processed in accordance with the grayscale mapping, the gain setting and the dynamic range setting currently stored in said memory;
(b) monitoring the state of said first control input device to detect a change in the state of said first control input device corresponding to activation of adaptive grayscale adjustment;
(c) in response to detection of such a change in the state of said first control input device, adjusting the contrast of said image frame by performing adaptive grayscale adjustment using the upper and lower grayscale levels currently stored in said memory, and controlling said display monitor to display said contrast-adjusted version of said image frame;
(d) monitoring the state of said second and third control input devices, during a first predetermined time period subsequent to said change in the state of said first control input device, to detect a change in the state of said second or third control input devices that results in a second gain setting different than said first gain setting or a second dynamic range setting different than said first dynamic range setting;
(e) in response to detection of such a change in the state of said second or third control input device, further adjusting the contrast of said image frame in accordance with said changed gain or dynamic range setting, and controlling said display monitor to display said further contrast-adjusted version of said image frame;
(f) monitoring the states of said second, third and fourth control input devices to detect whether either of the following conditions is satisfied: (i) the changed state of said second or third control input device is stabilized for a second predetermined time period immediately subsequent to said change in the state of said second or third control input device before any other system control change is made by the operator; or (ii) the state of said fourth control input device is changed to a state corresponding to activation of an image capture operation while the changed state of said second and/or third control input device is still in effect;
(g) if either of said conditions is satisfied, analyzing the pixel intensity histogram of said further contrast-adjusted version of said image frame to determine the operator-achieved upper and lower grayscale levels; and
(h) storing said operator-achieved upper and lower grayscale levels in said memory in place of the upper and lower grayscale levels used in step (c).

2. The imaging system as recited in claim 1, wherein said computer is further programmed to generate, during a subsequent adaptive grayscale adjustment, a gray map that is a function of said stored operator-achieved upper and lower grayscale levels.

3. The imaging system as recited in claim 1, wherein said computer is further programmed to store said operator-achieved upper and lower grayscale levels in association with a system user ID inputted via said operator interface.

4. The imaging system as recited in claim 3, wherein said computer is further programmed to store an application type or exam type in association with said operator-achieved upper and lower grayscale levels and said system user ID.

5. The imaging system as recited in claim 3, wherein said computer is further programmed to control said display monitor to display a message, prior to said storing step, requesting confirmation from the system user that operator-achieved upper and lower grayscale levels should be stored.

6. An imaging system comprising:
a display monitor;
an operator interface comprising a first control input device for activating adaptive grayscale adjustment, a second control input device for setting gain, a third control input device for setting dynamic range, and a fourth control input device for activating image capture;
a scanning subsystem for acquiring raw data; and
an image processing system for processing acquired raw data to display an image frame of imaging data on said display monitor, said image processing system comprising memory for storing displayed image frames, grayscale mappings, upper and lower grayscale levels for use in adaptive grayscale adjustment, gain settings, and dynamic range settings, and a computer programmed to perform the following steps:
(a) controlling said display monitor to display an image frame of imaging data derived from acquired raw data processed in accordance with the grayscale mapping, the gain setting and the dynamic range setting currently stored in said memory;
(b) monitoring the state of said first control input device to detect a change in the state of said first control input device corresponding to activation of adaptive grayscale adjustment;

(c) in response to detection of such a change in the state of said first control input device, adjusting the contrast of said image frame by performing adaptive grayscale adjustment using the upper and lower grayscale levels currently stored in said memory, and controlling said display monitor to display said contrast-adjusted version of said image frame;

(d) monitoring the state of said second and third control input devices, during a first predetermined time period subsequent to said change in the state of said first control input device, to detect a change in the state of said second or third control input devices that results in a second gain setting different than said first gain setting or a second dynamic range setting different than said first dynamic range setting;

(e) in response to detection of such a change in the state of said second or third control input device, further adjusting the contrast of said image frame in accordance with said changed gain or dynamic range setting, and controlling said display monitor to display said further contrast-adjusted version of said image frame;

(f) monitoring the states of said second, third and fourth control input devices to detect whether either of the following conditions is satisfied: (i) the changed state of said second or third control input device is stabilized for a second predetermined time period immediately subsequent to said change in the state of said second or third control input device before any other system control change is made by the operator; or (ii) the state of said fourth control input device is changed to a state corresponding to activation of an image capture operation while the changed state of said second and/or third control input device is still in effect;

(g) if either of said conditions is satisfied, analyzing the pixel intensity histogram of said further contrast-adjusted version of said image frame to determine the operator-achieved upper and lower grayscale levels; and (h) storing in said memory new upper and lower grayscale levels in place of the upper and lower grayscale levels used in step (c), said new upper and lower grayscale levels being a function of said operator-achieved upper and lower grayscale levels.

7. The imaging system as recited in claim 6, wherein said new upper grayscale level is an average of a first plurality of values, said first plurality including at least said upper grayscale level used in step (c) and said operator-achieved upper grayscale level, and said new lower grayscale level is an average of a second plurality of values, said second plurality including at least said lower grayscale level used in step (c) and said operator-achieved lower grayscale level.

8. The imaging system as recited in claim 6, wherein said computer is further programmed to store a system user ID in association with said operator-achieved upper and lower grayscale levels.

* * * * *